United States Patent

Komma et al.

[11] Patent Number: 5,281,563
[45] Date of Patent: Jan. 25, 1994

[54] DENTAL CERAMIC MATERIAL WITH A RELATIVELY LOW PROCESSING TEMPERATURE

[75] Inventors: Ottmar Komma, Niddatal; Juergen Steidl, Wöllstadt, both of Fed. Rep. of Germany

[73] Assignee: Degussa Aktiengesellschaft, Frankfurt am Main, Fed. Rep. of Germany

[21] Appl. No.: 979,644

[22] Filed: Nov. 20, 1992

[30] Foreign Application Priority Data

Nov. 27, 1991 [DE] Fed. Rep. of Germany ....... 4138875

[51] Int. Cl.$^5$ ............................................. C03C 3/091
[52] U.S. Cl. ........................................ 501/59; 106/35; 501/66; 501/70; 501/72; 501/2
[58] Field of Search ................ 106/35; 501/59, 66, 501/72, 70, 2

[56] References Cited

U.S. PATENT DOCUMENTS

| 4,431,451 | 2/1984 | Mabie et al. | 106/35 |
| 5,009,709 | 4/1991 | Ibsen et al. | 106/35 |

FOREIGN PATENT DOCUMENTS

| 0475528 | 3/1992 | European Pat. Off. |
| 0478937 | 4/1992 | European Pat. Off. |
| 3911460 | 10/1990 | Fed. Rep. of Germany |
| 2313912 | 1/1977 | France |

*Primary Examiner*—Mark L. Bell
*Assistant Examiner*—C. M. Bonner
*Attorney, Agent, or Firm*—Beveridge, DeGrandi, Weilacher & Young

[57] ABSTRACT

A dental ceramic material is disclosed for the preparation and repair of metal ceramic and fully ceramic dentures, which has a processing temperature of 660±30° C., and has the following composition: 60 to 65% by weight of $SiO_2$, 8.5 to 11% by weight of $Al_2O_3$, 8 to 12% by weight of $K_2O$, 10.5 to 12% by weight of $Na_2O$, 0.7 to 2% by weight of CaO, 0.6 to 2% by weight of BaO, 0.5 to 2.5% by weight of $B_2O_3$, 0.1 to 0.6% by weight of $Sb_2O_3$, 0 to 0.5% by weight of $CeO_2$, 1.2 to 3.8% by weight of $TiO_2$, 0.8 to 1.4% by weight of $Li_2O$, and 1.2 to 3.8% by weight of $F_2$.

7 Claims, No Drawings

DENTAL CERAMIC MATERIAL WITH A RELATIVELY LOW PROCESSING TEMPERATURE

INTRODUCTION AND BACKGROUND

The present invention relates to a dental ceramic material for the preparation and repair of metal ceramic and fully ceramic dentures with a processing temperature below 700° C. and a coefficient of thermal expansion $\alpha$ of $13-14 \cdot 10^{-6} \cdot K^{-1}$ between 20° and 500° C.

Using dental ceramic materials, it is possible to prepare fully ceramic dentures, to carry out modifications to change the shape of metal ceramic and fully ceramic dentures, to repair damaged sections or to line metallic dentures with a ceramic layer.

For many years ceramic layers have been used in dentistry for lining metallic frameworks (crowns, bridges), using a type of enamelling, in order to give the denture a natural appearance. In this case, ceramic powders are applied to the metallic framework as an aqueous slurry and fired at elevated temperatures. It is important here that the firing temperature (processing temperature) of the ceramic body is at least 100° C. below the solidus temperature of the material in the metallic framework and that the coefficient of thermal expansion of the ceramic body in the range 20° to 500° C. is only very slightly less than that of the metallic material, so that no cracks are produced in the lining layer during firing and cooling down.

In the same way as these so-called metal ceramic dentures, fully ceramic dental items such as full crowns, part crowns, temporary fillings and lining shells may be prepared in sinter processes, using the same ceramic materials on refractory ceramic molding materials.

Dental ceramics of this type, for lining, generally require high coefficients of thermal expansion, which should be 13 to $14 \cdot 10^{-6} \cdot K^{-1}$ between 20° and 500° C., due to the material in the metallic framework. Normally, these ceramics are processed at 950° ± 30° C., but this is too high for some dental alloys. It is very difficult to lower the processing temperature significantly by altering the composition of the dental ceramics without adversely altering the coefficients of thermal expansion and resistance to corrosion. Furthermore, biologically suspect components, such as e.g. lead oxide, must be avoided.

Coefficients of thermal expansion of $13-14 \cdot 10^{-6} \cdot K^{-1}$ between 20° and 500° C. are generally only achieved if the dental ceramic materials contain 25 to 30% by weight of alkali metal oxides. However, in an acid environment, such as e.g. in oral cavities under plaque, this means that the limit of resistance to corrosion of these ceramics is reached.

DE-OS 39 11 460 discloses dental ceramic materials for the preparation, correction and repair of metal ceramic and fully ceramic dentures, which contain, apart from $SiO_2$ as the balance, 5–15% $Al_2O_3$, 0.5–2.5% $B_2O_3$, 0.5–2.5% $Sb_2O_3$, 0.1–0.5% CaO, 0.5–2.5% BaO, 5–10% $Na_2O$, 10–15% $K_2O$, 0.1–0.5% $Li_2O$ and 0.1–0.5% $F_2$. These actually have coefficients of thermal expansion of $13.5 (\pm 1) \cdot 10^{-6} \cdot K^{-1}$ between 20° and 500° C., but their processing temperatures of 730° ± 30° C. are still too high for some dental alloys during lining.

In German Patent Application p 40 31 168.6, which has not been published previously, ceramic materials for lining metallic dentures, which have a coefficient of thermal expansion of $16-17.5 \cdot 10^{-6} \cdot K^{-1}$ and a processing temperature of 770° ± 70° C., are described. They consist of 60 to 68% $SiO_2$, 10 to 15% $Al_2O_3$, 0.7 to 1.5% $B_2O_3$, 0 to 0.5% $Sb_2O_3$, 0 to 0.5% $CeO_2$, 0 to 0.5% BaO, 0.1 to 0.5% CaO, 9 to 12% $K_2O$, 9 to 11% $Na_2O$, 0.8 to 1.4% $Li_2O$ and 0.2 to 0.4% $F_2$.

SUMMARY OF THE INVENTION

An object of the present invention was to develop a dental ceramic material for the preparation and repair of metal ceramic and fully ceramic dentures, which has a coefficient of thermal expansion of 13 to $14 \cdot 10^{-6} \cdot K^{-1}$ between 20° and 500° C. and a processing temperature below 700° C. In addition, it should contain no biologically suspect components and be resistant to corrosion in the mouth.

The present invention discloses a material which consists of 60 to 65% by weight of $SiO_2$, 8.5 to 11% by weight of $Al_2O_3$, 8 to 12% by weight of $K_2O$, 10.5 to 12% by weight of $Na_2O$, 0.7 to 2% by weight of CaO, 0.6 to 2% by weight of BaO, 0.5 to 2.5% by weight of $B_2O_3$, 0.1 to 0.6% by weight of $Sb_2O_3$, to 0.5% by weight of $CeO_2$, 1.2 to 3.8% by weight of $TiO_2$, 0.8 to 1.4% by weight of $Li_2O$ and 1.2 to 3.8% by weight of $F_2$.

The present invention also discloses a method of using the dental ceramic material described herein and to a dental prosthesis comprising a metal ceramic denture or ceramic denture and the dental ceramic material described herein.

DETAILED DESCRIPTION OF THE INVENTION

Preferably the dental ceramic materials contain 60 to 63% by weight of $SiO_2$, 8.5 to 9.5% by weight of $Al_2O_3$, 10 to 11.5% by weight of $K_2O$, 10.5 to 11.5% by weight of $Na_2O$, 0.7 to 1.5% by weight of CaO, 0.6 to 1.2% by weight of BaO, 0.7 to 1.5% by weight of $B_2O_3$, 0.2 to 0.4% by weight of $Sb_2O_3$, 0.1 to 0.4% by weight of $CeO_2$, 1.5 to 3% by weight of $TiO_2$, 0.8 to 1.2% by weight of $Li_2O$ and 1.2 to 2.4% by Weight of $F_2$.

The dental ceramic materials according to the present invention have processing temperatures of 660° ± 30° C. The glass point is about 450° C. and the softening point is about 510° C. They possess very high material homogeneity and a very high transparency (more than 70% light transmission). The resistance to bending according to DIN 13925 is 110 $N \cdot mm^{-2}$ and is therefore far above their minimum requirement of 50 $N \cdot mm^{-2}$.

The loss in mass during resistance to corrosion testing according to DIN 13925 (16 hours in 4% acetic acid) is about 0.028% by weight. Surprisingly, the resistance to bending is then increased by up to 50%, whereas it decreases by up to 30% with known dental ceramics.

The following Table reproduces the composition of some particularly advantageous materials:

| Material | 1 | 2 | 3 |
| --- | --- | --- | --- |
| $SiO_2$ | 61.3% | 60.9 | 62.3 |
| $Al_2O_3$ | 9.0% | 8.6 | 9.3 |
| $K_2O$ | 10.7% | 11.2 | 10.2 |
| $Na_2O$ | 10.9% | 10.7 | 12.0 |
| CaO | 1.0% | 0.9 | 0.8 |
| BaO | 0.9% | 0.7 | 0.8 |
| $B_2O_3$ | 1.0% | 1.8 | 0.5 |
| $Sb_2O_3$ | 0.3% | 0.2 | 0.1 |
| $CeO_2$ | 0.2% | 0.3 | 0.1 |
| $TiO_2$ | 2.1% | 1.2 | 1.3 |
| $Li_2O$ | 1.0% | 0.8 | 1.4 |

| Material | 1 | 2 | 3 |
|---|---|---|---|
| F$_2$ | 1.6% | 2.7 | 1.2 |

The present invention also concerns a method of making dental prosthesis using the dental material described above and utilizing methods known in the art to form dental prosthesis. The present invention further concerns a dental prothesis, dental bridge, dental crown or other dental items formed from the material described above by methods known in the art. U.S. Pat. No. 4,562,882 is incorporated by reference in its entirety.

Further variations and modifications of the invention will become apparent to those skilled in the art from the foregoing and are intended to be encompassed by the claims appended hereto.

What is claimed:

1. A dental ceramic material for the preparation and repair of metal ceramic and fully ceramic dentures said material having a processing temperature below 700° C. and a coefficient of thermal expansion $\alpha$ of $13-14 \cdot 10^{-6} \cdot K^{-1}$ between 20° and 500° C., said material comprising 60 to 65% by weight of SiO$_2$, 8.5 to 11% by weight of Al$_2$O$_3$, 8 to 12% by weight of K$_2$O, 10.5 to 12% by weight of Na$_2$O, 0.7 to 2% by weight of CaO, 0.6 to 2% by weight of BaO, 0.5 to 2.5% by weight of B$_2$O$_3$, 0.1 to 0.6% by weight of Sb$_2$O$_3$, 0 to 0.5% by weight of CeO$_2$, 1.2 to 3.8% by weight of TiO$_2$, 0.8 to 1.4% by weight of Li$_2$O and 1.2 to 3.8% by weight of F$_2$.

2. The dental ceramic material according to claim 1, said material comprising 60 to 63% by weight of SiO$_2$, 8.5 to 9.5% by weight of Al$_2$O$_3$, 10 to 11.5% by weight of K$_2$O, 10.5 to 11.5% by weight of Na$_2$O, 0.7 to 1.5% by Weight of CaO, 0.6 to 1.2% by weight of BaO, 0.7 to 1.5% by weight of B$_2$O$_3$, 0.2 to 0.4% by weight of Sb$_2$O$_3$, 0.1 to 0.4% by weight of CeO$_2$, 1.5 to 3% by weight of TiO$_2$, 0.8 to 1.2% by weight of Li$_2$O and 1.2 to 2.4% by weight of F$_2$.

3. The dental ceramic material according to claim 1, wherein said material has a processing temperature of 660°±30° C.

4. The dental ceramic material according to claim 1, wherein said material has a glass point of about 450° C. and a softening point of about 510° C.

5. The dental ceramic material according to claim 1, said material comprising: 61.3% by weight of SiO$_2$, 9% by weight of Al$_2$O$_3$, 10.7% by weight of K$_2$O, 10.9% by weight of Na$_2$O, 1.0% by weight of CaO, 0.9% by weight of BaO, 1.0% by weight of B$_2$O$_3$, 0.3% by weight of Sb$_2$O$_3$, 0.2% by weight of CeO$_2$, 2.1% by weight of TiO$_2$, 1.0% by weight of Li$_2$O and 1.6% by weight of F$_2$.

6. The dental ceramic material according to claim 1, said material comprising: 60.9% by weight of SiO$_2$, 8.6% by weight of Al$_2$O$_3$, 11.2% by weight of K$_2$O, 10.7% by weight of Na$_2$O, 0.9% by weight of CaO, 0.7% by weight of BaO, 1.8% by weight of B$_2$O$_3$, 0.2% by weight of Sb$_2$O$_3$, 0.3% by weight of CeO$_2$, 1.2% by weight of TiO$_2$, 0.8% by weight of Li$_2$O and 2.7% by weight of F$_2$.

7. The dental ceramic material according to claim 1, said material comprising: 62.3% by weight of SiO$_2$, 9.3% by weight of Al$_2$O$_3$, 10.2% by weight of D$_2$O, 12.0% by weight of Na$_2$O, 0.8% by weight of CaO, 0.8% by weight of BaO, 0.5% by weight of B$_2$O$_3$, 0.1% by weight of Sb$_2$O$_3$, 0.1% by weight of CeO$_2$, 1.3% by weight of TiO$_2$, 1.4% by weight of Li$_2$O and 1.2% by weight of F$_2$.

* * * * *